US006933418B2

(12) United States Patent
Kelly et al.

(10) Patent No.: US 6,933,418 B2
(45) Date of Patent: Aug. 23, 2005

(54) CRITICAL PHASE ALKYLATION PROCESS

(75) Inventors: Kevin P Kelly, Friendswood, TX (US); James R. Butler, Webster, TX (US)

(73) Assignee: Fina Technology, Inc., Houston, TX (US)

(*) Notice: Subject to any disclaimer, the term of this patent is extended or adjusted under 35 U.S.C. 154(b) by 0 days.

(21) Appl. No.: 10/268,390

(22) Filed: Oct. 4, 2002

(65) Prior Publication Data

US 2004/0068151 A1 Apr. 8, 2004

(51) Int. Cl.[7] .................................................. C07C 2/66
(52) U.S. Cl. ........................ 585/467; 585/475; 585/323
(58) Field of Search ................................. 585/467, 475, 585/323

(56) References Cited

U.S. PATENT DOCUMENTS 4,891,458 A * 1/1990 Innes et al. ................. 585/323

\* cited by examiner

Primary Examiner—Thuan D. Dang
(74) Attorney, Agent, or Firm—William D. Jackson

(57) ABSTRACT

A process for the production of ethylbenzene by the ethylation of benzene in the critical phase over a molecular sieve aromatic alkylation catalyst comprising cerium-promoted zeolite beta. An aromatic feedstock having a benzene content of at least 90 wt. % is supplied into a reaction zone and into contact with the cerium-promoted zeolite beta having a silica/alumina mole ratio within the range of 50–150 and a cerium-aluminum ratio of 0.5–1.5. Ethylene is supplied to the alkylation reaction zone in an amount to provide a benzene/ethylene mole ratio of 1–15. The reaction zone is operated at temperature and pressure conditions in which benzene is in the super critical phase to cause ethylation of the benzene in the presence of the cerium zeolite beta alkylation catalyst. An alkylation product is produced containing ethylbenzene as a primary product with the attendant production of heavier alkylated by-products of no more than 60 wt. % of the ethylbenzene. The critical phase alkylation reaction may be followed by the transalkylation of a polyalkylated aromatic component.

20 Claims, 7 Drawing Sheets

CRITICAL PHASE ALKYLATION PROCESS

FIELD OF THE INVENTION

This invention relates to the production of ethylbenzene and more particularly to the ethylation of benzene over a cerium-promoted beta alkylation catalyst under the conditions in which the benzene is in the supercritical phase.

BACKGROUND OF THE INVENTION

The alkylation of benzene with ethylene over a molecular sieve catalyst is a well-known procedure for the production of ethylbenzene. Typically, the alkylation reaction is carried out in a multistage reactor involving the interstage injection of ethylene and benzene to produce an output from the reactor that involves a mixture of monoalkyl and polyalkylbenzene. The principal monoalkylbenzene is, of course, the desired ethylbenzene product. Polyalkylbenzenes include diethylbenzene, triethylbenzene, and xylenes.

In many cases, it is desirable to operate the alkylation reactor in conjunction with the operation of a transalkylation reactor in order to produce additional ethylbenzene through the transalkylation reaction of polyethylbenzene with benzene. The alkylation reactor can be connected to the transalkylation reactor in a flow scheme involving one or more intermediate separation stages for the recovery of ethylene, ethylbenzene, and polyethylbenzene.

Transalkylation may also occur in the initial alkylation reactor. In this respect, the injection of ethylene and benzene between stages in the alkylation reactor not only results in additional ethylbenzene production but also promotes transalkylation within the alkylation reactor in which benzene and diethylbenzene react through a disproportionation reaction to produce ethylbenzene.

Various phase conditions may be employed in the alkylation and transalkylation reactors. Typically, the transalkylation reactor will be operated under liquid phase conditions, i.e., conditions in which the benzene and polyethylbenzene are in the liquid phase, and the alkylation reactor is operated under gas phase conditions, i.e., pressure and temperature conditions in which the benzene is in the gas phase. However, liquid phase conditions can be used where it is desired to minimize the yield of undesirable by-products from the alkylation reactor.

SUMMARY OF THE INVENTION

In accordance with the present invention, there is provided a process for the production of ethylbenzene by the ethylation of benzene in the critical phase over a molecular sieve aromatic alkylation catalyst comprising cerium-promoted zeolite beta. In one aspect of the invention, an aromatic feedstock having a benzene content of at least 90 wt. % is supplied into a reaction zone and into contact with the cerium-promoted zeolite beta. Preferably the zeolite beta has a silica/alumina mole ratio within the range of 20–500 and more, preferably within the range of 50–150. Ethylene is supplied to the alkylation reaction zone in an amount to provide a benzene/ethylene mole ratio of 1–15. The reaction zone is operated at temperature and pressure conditions in which benzene is in the super critical phase to cause ethylation of the benzene in the presence of the zeolite beta alkylation catalyst. An alkylation product is produced containing ethylbenzene as a primary product with the attendant production of heavier alkylated by-products of no more than 60 wt. % of the ethylbenzene. The alkylation product is recovered from the reaction zone for further use or processing. Preferably, the alkylation reaction zone is operated under temperature and pressure conditions providing a composite by-product yield of propyl benzene and butyl benzene relative to ethylbenzene, which is no more than one-half of the corresponding yield by-product for zeolite beta promoted with lanthanum.

In a further aspect of the invention, there is provided a process for the production of ethylbenzene in a critical phase alkylation reaction zone followed by the transalkylation of a polyalkylated aromatic component. In this aspect of the invention, there is provided an alkylation reaction zone containing cerium-promoted beta aromatic alkylation catalyst. A feedstock containing benzene in an amount of at least 95 wt. % of the aromatic content of the feedstock as a major component and ethylene as a minor component is supplied to the alkylation reaction zone. The alkylation reaction zone is operated at temperature and pressure conditions at which benzene is in the super critical phase to cause ethylation of the benzene in the presence of the cerium-promoted zeolite beta and to produce an alkylation product comprising a mixture of benzene, ethylbenzene, and polyalkylated aromatics, including diethylbenzene. The alkylation product is recovered from the alkylation reaction zone and supplied to a separation and recovery zone. In the recovery zone, ethylbenzene is separated and recovered from the product as well as the separation of a polyalkylated component including diethylbenzene. At least a portion of the polyalkylated aromatic component, including diethylbenzene, is supplied to a transalkylation reaction zone containing a molecular sieve transalkylation catalyst. Benzene is also supplied to the transalkylation reaction zone, and the transalkylation reaction zone is operated under temperature and pressure conditions to cause disproportionation of the polyalkylated aromatic fraction to produce a disproportionation product having a reduced diethylbenzene content and an enhanced ethylbenzene content. Preferably, the transalkylation reaction zone contains a zeolite Y catalyst and is operated under conditions to maintain the polyalkylated aromatic component in the liquid phase. Preferably, the cerium-promoted zeolite beta has a silica/alumina ratio within the range of 50–150 and a cerium/aluminum ratio within the range of 0.25–5.0, preferably 0.5–1.5.

The cerium-promoted zeolite beta only gradually undergoes deactivation and as a result can be employed for prolonged periods of time before regeneration is necessary. In regenerating the catalyst, the regeneration procedure is initiated by injecting an inert oxygen-free gas, such as nitrogen, initially into the catalyst bed. The initial nitrogen injection step is carried out at any suitable temperature, normally about 300–310° C., and is continued until the benzene in the bed is depleted and the catalyst bed is essentially dry. Thereafter, oxygen is added to the nitrogen stream. Typically, this is accomplished by gradually adding air in increasing amounts while gradually decreasing nitrogen injection until only air is injected. The oxygen burns coke off the catalyst, and the temperature gradually increases until an exotherm is measured. When the temperature then decreases and falls off, normally to a value near the initial temperature, e.g. 300–310° C., air injection is terminated and hot nitrogen is then injected for a suitable period of time to provide an incremental increase of perhaps 50–100° C. Air injection is then reinstituted while progressively lessening nitrogen injection, and the process is carried out until an exotherm is reached and the temperature within the catalyst bed reaches a maximum and then decreases to a value approximately that of the catalyst bed at the termination of the previous air injection step. Air injection is terminated and hot nitrogen injection is reinstituted, and the procedure is reached until the temperature in the catalyst bed ultimately reaches a level of at least 500° C., preferably in excess of 510° C. Typically, the regeneration procedure is carried to its conclusion at a final exotherm having a temperature within the range of about 525–550° C. The catalyst regenerated by this mode of operation exhibits a relatively gradual deactivation characteristic similar to that exhibited by the initial fresh cerium-promoted zeolite beta.

DETAILED DESCRIPTION OF THE INVENTION

Figure 1:
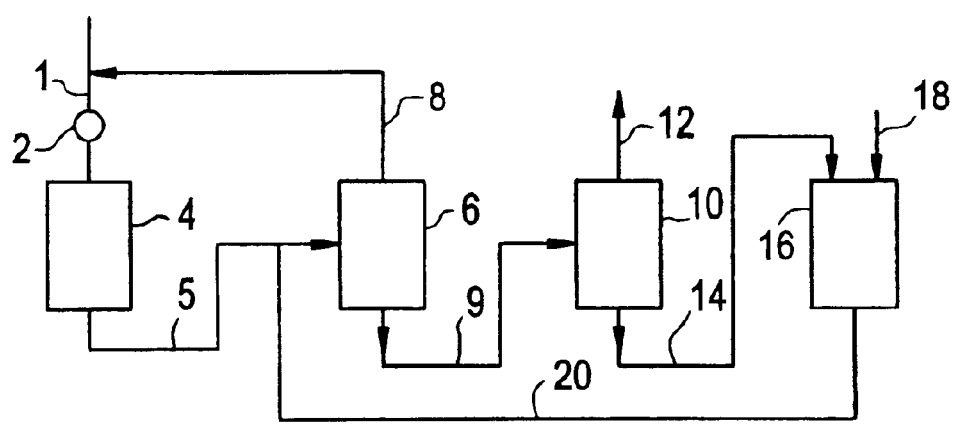
FIG. 1 is an idealized schematic block diagram of an alkylation/transalkylation process embodying the present invention.

The present invention involves the critical phase alkylation of benzene over a cerium-promoted zeolite beta alkylation catalyst under conditions to control and desirably minimize the yield of by-products in the alkylation reaction zone. The feedstock supplied to the alkylation reaction zone comprises benzene and ethylene. Typically, the benzene and ethylene streams will be combined to provide a benzene-ethylene mixture into the reaction zone. The benzene stream, which is mixed with the ethylene either before or after introduction into the reaction zone, should be a relatively pure stream containing only very small amounts of contaminants. The benzene stream should contain at least 90 wt. % benzene. Preferably, the benzene stream will be at least 98 wt. % benzene with only trace amounts of such materials as toluene, ethylbenzene, and $C_7$ aliphatic compounds that cannot readily be separated from benzene. The alkylation reaction zone is operated under supercritical conditions, that is, pressure and temperature conditions which are above the critical pressure and critical temperature of benzene. Specifically, the temperature in the alkylation zone is at or above 310° C., and the pressure is at or above 550 psia. Preferably, the temperature in the alkylation reactor will be maintained at an average value within the range of 320–350° C. and a pressure within the range of 550–850 psia. If desired higher alkylation temperatures can be employed since the cerium-promoted zeolite beta retains its structural integrity at temperatures of about 530–540° C. Zeolite beta which has not been promoted with cerium tends to lose its structural integrity as the temperature reaches 500° C. The critical phase alkylation reaction is exothermic with a positive temperature gradient from the inlet to the outlet of the reactor, providing a temperature increment increase of about 40° C.±10°.

The operation of the alkylation reaction zone in the supercritical region enables the alkylation zone to be operated under conditions in which the benzene-ethylene mole ratio can be maintained at relatively low levels, usually somewhat lower than the benzene-ethylene mole ratio encountered when the alkylation reaction zone is operated under liquid phase conditions. In most cases, the benzene-ethylene mole ratio will be within the range of 1–15. Preferably, the benzene mole ratio will be maintained during at least part of a cycle of operation at a level within the lower end of this range, specifically, at a benzene-ethylene mole ratio of less than 10. A benzene-ethylene mole ratio within the range of 3–8 may be employed. Thus, operation in the supercritical phase offers the advantages of gas phase alkylation in which the benzene-ethylene ratio can be kept low but without the problems associated with by-product formation, specifically xylene formation, often encountered in gas-phase alkylation. At the same time, operation in the super critical phase offers the advantages accruing to liquid phase alkylation in which the by-product yield is controlled to low levels. The pressures required for operation in the super critical phase are not substantially greater than those required in liquid phase alkylation, and the benzene in the supercritical phase functions as a solvent to keep the zeolite beta catalyst clean and to retard coking leading to deactivation of the catalyst.

As indicated by the experimental work described later, the cerium-promoted beta enables super critical phase alkylation to be carried out with by-products that are substantially less than the corresponding by-products produced with super critical phase alkylation employing lanthanum-promoted zeolite beta of similar or greater content. Thus, the alkylation reaction zone can be operated at super critical phase temperature and pressure conditions to provide a composite by-product yield of propylbenzene and butylbenzene which is less than the corresponding composite by-product yield of propylbenzene and butylbenzene for a corresponding zeolite beta catalyst promoted with lanthanum at a lanthanum/beta atomic ratio at least as great as the cerium/aluminum atomic ratio of the cerium-promoted zeolite beta. Preferably, the alkylation reaction zone is operated at temperature and pressure conditions to provide a composite product yield of propylbenzene and butylbenzene which is no more than one-half of the corresponding composite by-product yield of propylbenzene and butylbenzene produced with the lanthanum-promoted zeolite beta.

Turning now to FIG. 1, there is illustrated a schematic block diagram of an alkylation/transalkylation process employing the present invention. As shown in FIG. 1, a product stream comprising a mixture of ethylene and benzene in a mole ratio of benzene to ethylene of about 1 to 15 is supplied via line 1 through a heat exchanger 2 to an alkylation reaction zone. Alkylation zone 4 preferably comprises one or more multi-stage reactors having a plurality of series-connected catalyst beds containing a cerium zeolite beta alkylation catalyst as described herein. The alkylation zone 4 is operated at temperature and pressure conditions to maintain the alkylation reaction in the supercritical phase, i.e. the benzene is in the supercritical state, and at a feed rate to provide a space velocity enhancing diethylbenzene production while retarding by-products production. Preferably, the space velocity of the benzene feed stream will be within the range of 10–150 hrs.$^{-1}$ LHSV per bed.

The output from the alkylation reactor 4 is supplied via line 5 to an intermediate benzene separation zone 6 that may take the form of one or more distillation columns. Benzene is recovered through line 8 and recycled through line 1 to the alkylation reactor. The bottoms fraction from the benzene separation zone 6, which includes ethylbenzene and polyalkylated benzenes including polyethylbenzene, is supplied via line 9 to an ethylbenzene separation zone 10. The ethylbenzene separation zone may likewise comprise one or more sequentially connected distillation columns. The ethylbenzene is recovered through line 12 and applied for any suitable purpose, such as in the production of vinyl benzene. The bottoms fraction from the ethylbenzene separation zone 10, which comprises polyethylbenzene, principally diethylbenzene, is supplied via line 14 to a transalkylation reactor 16. Benzene is supplied to the transalkylation reaction zone through line 18. The transalkylation reactor, which preferably is operated under liquid phase conditions, contains a molecular sieve catalyst, preferably zeolite-Y, which has a somewhat larger pore size than the cerium-modified zeolite beta used in the reaction alkylation zone. The output from the transalkylation reaction zone is recycled via line 20 to the benzene separation zone 6.

Figure 2:
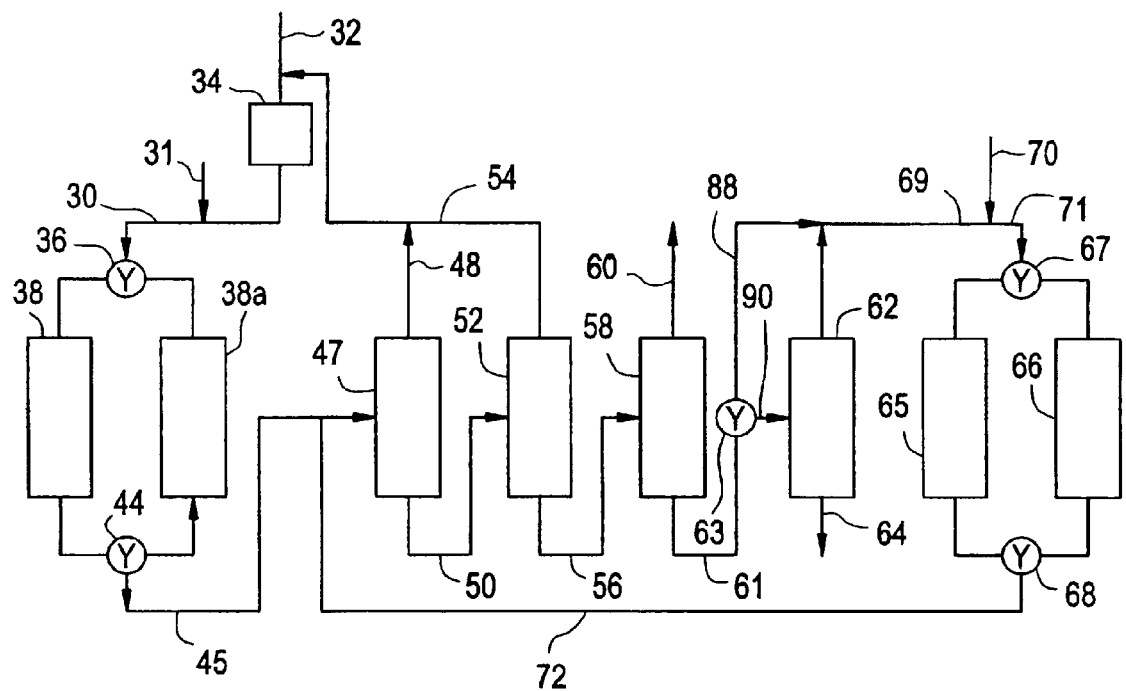
FIG. 2 is a schematic illustration of a preferred embodiment of the invention incorporating separate parallel-connected alkylation and transalkylation reactors with an intermediate multi-stage recovery zone for the separation and recycling of components.

Referring now to FIG. 2, there is illustrated in greater detail a suitable system incorporating a multi-stage intermediate recovery zone for the separation and recycling of components involved in the critical phase alkylation and transalkylation process. As shown in FIG. 2, an input feed stream is supplied by fresh ethylene through line 31 and fresh benzene through line 32. As noted previously, the fresh benzene stream supplied via line 32 preferably is of high purity containing at least 98 wt. %, preferably about 99 wt. %, benzene with no more than 1 wt. % other components. Typically, the fresh benzene stream will contain about 99.5 wt. % benzene, less than 0.5% ethylbenzene, with only trace amounts of non-aromatics and toluene. Line 32 is provided with a preheater 34 to heat the benzene stream consisting of fresh and recycled benzene to the desired temperature for the supercritical alkylation reaction. The feed stream is supplied through a two-way, three-position valve 36 and inlet line 30 to the top of one or both parallel critical phase alkylation reactor 38 and 38A comprising a plurality of series connected catalyst beds each of which contains the desired molecular sieve alkylation catalyst. The reactors are operated at an average temperature, preferably within the range of 300°–350° C. inlet temperature and at pressure conditions of about 650 to 800 psia, to maintain the benzene in the critical phase. As mentioned previously, because of the high temperature structural integrity of cerium-promoted zeolite beta, the alkylation reaction zone can be operated at temperatures of up to about 500° C. and even beyond that to temperatures of about 540° C.

In normal operation of the system depicted in FIG. 2, both reaction zones 38 and 38A may, during most of a cycle of operation, be operated in a parallel mode of operation in which they are both in service at the same time. In this case, valve 36 is configured so that the input stream in line 30 is roughly split in two to provide flow to both reactors in approximately equal amounts. Periodically, one reactor can be taken off-stream for regeneration of the catalyst. Valve 36 is then configured so that all of the feed stream from line 30 can be supplied to reactor 38 while the catalyst beds in reactor 38A are regenerated and visa versa. The regeneration procedure will be described in detail below but normally will take place over a relatively short period of time relative to the operation of the reactor in parallel alkylation mode. The regeneration procedure preferably is carried out at temperatures substantially in excess of those normally employed in the regeneration of zeolite beta-type catalysts. When regeneration of the catalyst beds in reactor 38A is completed, this catalyst can then be returned on-stream, and at an appropriate point, the reactor 38 can be taken off-stream for regeneration. This mode of operation involves operation of the individual reactors at relatively lower space velocities for prolonged periods of time with periodic relatively short periods of operation at enhanced, relatively higher space velocities when one reactor is taken off-stream. By way of example, during normal operation of the system with both reactors 38 and 38A on-stream, the feed stream is supplied to each reactor to provide a space velocity of about 25–45 hr.$^{-1}$ LHSV. When reactor 38A is taken off-stream and the feed rate continues unabated, the space velocity for reactor 38 will approximately double to 50–90 hr.$^{-1}$ LHSV. When the regeneration of reactor 38A is completed, it is placed back on-stream, and again the feed stream rate space velocity for each reactor will decrease to 25–45 hr.$^{-1}$ until such point as reactor 38 is taken off-stream, in which case the flow rate to reactor 38A will, of course, increase, resulting again in a transient space velocity in reactor 38 of about 50–90 hr$^{-1}$ LHSV.

Figure 3:
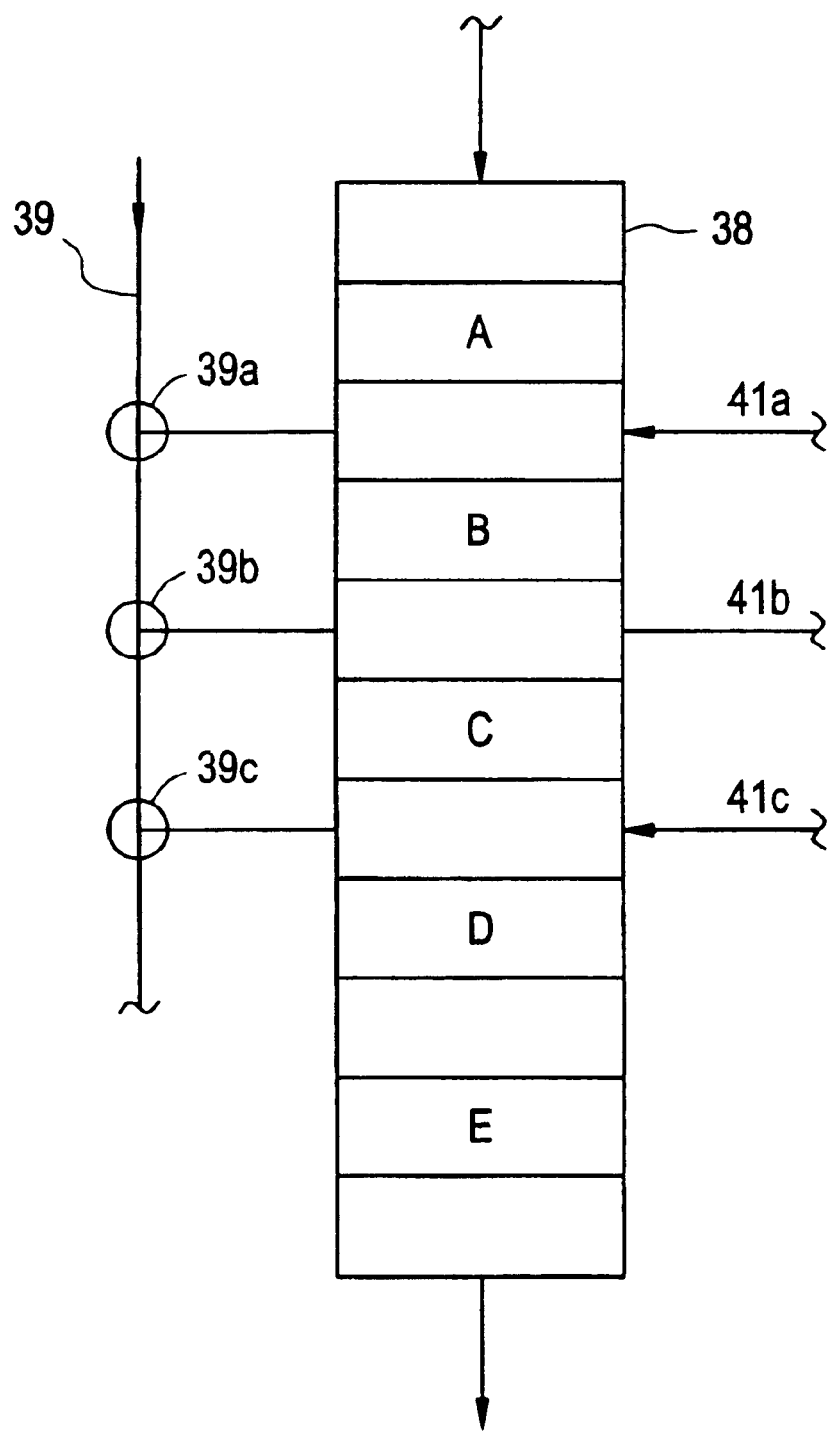
FIG. 3 is a schematic illustration of an alkylation reactor comprising a plurality of series connected catalyst beds with the interstate injection of feed components.

A preferred reactor configuration is shown in detail in FIG. 3. As illustrated there, the reactor 38 comprises five series connected catalyst beds designated as beds A, B, C, D, and E. A benzene-ethylene feed stream is supplied to the top of the reactor and into Bed A. An ethylene feed stream is supplied via line 39 and proportionating valves 39a, 39b and 39c to provide for the appropriate interstage injection of ethylene. Benzene can also be introduced between the catalyst stages by means of secondary benzene supply lines 41a, 41b and 41c, respectively. As will be recognized, the parallel reactor 38A will be configured with similar manifolding as shown in FIG. 3 with respect to reactor 38.

Returning to FIG. 2, the effluent stream from one or both of the alkylation reactors 38 and 38A is supplied through a two-way, three-position outlet valve 44 and outlet line 45 to a two-stage benzene recovery zone which comprises as the first stage a prefractionation column 47. Column 47 is operated to provide a light overhead fraction including benzene which is supplied via line 48 to the input side of heater 34 where it is mixed with benzene in line 32 and then to the alkylation reactor input line 30. A heavier liquid fraction containing benzene, ethylbenzene and polyethylbenzene is supplied via line 50 to the second stage 52 of the benzene separation zone. Stages 47 and 52 may take the form of distillation columns of any suitable type, typically, columns having from about 20–60 trays. The overhead fraction from column 52 contains the remaining benzene, which is recycled via line 54 to the alkylation reactor input. Thus, lines 48 and 54 correspond to the output line 8 of FIG. 1. The heavier bottoms fraction from column 52 is supplied via line 56 to a secondary separation zone 58 for the recovery of ethylbenzene. The overhead fraction from column 58 comprises relatively pure ethylbenzene, which is supplied to storage or to any suitable product destination by way of line 60. By way of example, the ethylbenzene may be used as a feed stream to a styrene plant in which styrene is produced by the dehydrogenation of ethylbenzene. The bottoms fraction containing polyethylbenzenes, heavier aromatics such as cumene and butyl benzene, and normally only a small amount of ethylbenzene is supplied through line 61 to a tertiary polyethylbenzene separation zone 62. As described below, line 61 is provided with a proportioning valve 63 which can be used to divert a portion of the bottoms fraction directly to the transalkylation reactor. The bottoms fraction of column 62 comprises a residue, which can be withdrawn from the process via line 64 for further use in any suitable manner. The overhead fraction from column 62 comprises a polyalkylated aromatic component containing diethylbenzene and a smaller amount of triethylbenzene and a minor amount of ethylbenzene is supplied to an on stream transalkylation reaction zone. Similarly as described above with respect to the alkylation reactors, parallel transalkylation reactors 65 and 66 are provided through inlet and outlet manifolding involving valves 67 and 68. Both of reactors 65 and 66 can be placed on stream at the same time so that both are in service in a parallel mode of operation. Alternatively, only one transalkylation reactor can be on-stream with the other undergoing regeneration operation in order to burn coke off the catalyst beds. By minimizing the amount of ethylbenzene recovered from the bottom of column 58, the ethylbenzene content of the transalkylation feed stream can be kept small in order to drive the transalkylation reaction in the direction of ethylbenzene production. The polyethylbenzene fraction withdrawn overhead from column 62 is supplied through line 69 and mixed with benzene supplied via line 70. This mixture is then supplied to the on-line transalkylation reactor 65 via line 71. Preferably, the benzene feed supplied via line 70 is of relatively low water content, about 0.05 wt. % or less. Preferably, the water content is reduced to a level of about 0.02 wt. % or less and more preferably to less than 0.01 wt. %, down to 0.002 wt. % or less. The transalkylation reactor is operated as described before in order to maintain the benzene and alkylated benzenes within the transalkylation reactor in the liquid phase. Typically, the transalkylation reactor may be operated to provide an average temperature within the transalkylation reactor of about 65°–290° C. and an average pressure of about 600 psi. The preferred catalyst employed in the transalkylation reactor is zeolite Y. The weight ratio of benzene to polyethylbenzene should be at least 1:1 and preferably is within the range of 1:1 to 4:1.

The output from the transalkylation reactor or reactors containing benzene, ethylbenzene, and diminished amounts of polyethylbenzene is recovered through line 72. Typically, line 72 will be connected to the inlet lines 47a for recycle to the prefractionation column 47 as shown. However, the effluent from the liquid-phase transalkylation reactor may be supplied to either or both of distillation columns 47 and 52.

Returning to the operation of the separation system, in one mode of operation the entire bottoms fraction from the ethylbenzene separation column 58 is applied to the tertiary separation column 62 with overhead fractions from this zone then applied to the transalkylation reactor. This mode of operation offers the advantage of relatively long cycle lengths of the catalyst in the transalkylation reactor between regeneration of the catalyst to increase the catalyst activity. Another mode of operation of the invention achieves this advantage by supplying a portion of the output from the ethylbenzene separation column 58 through valve 63 directly to the transalkylation reactor.

As shown in FIG. 2, a portion of the bottoms fraction from the secondary separation zone 58 bypasses column 62 and is supplied directly to the transalkylation reactor 65 via valve 63 and line 88. A second portion of the bottoms fraction from the ethylbenzene column is applied to the tertiary separation column 62 through valve 63 and line 90. The overhead fraction from column 62 is commingled with the bypass effluent in line 88 and the resulting mixture is fed to the transalkylation reactor via line 67. In this mode of operation a substantial amount of the bottoms product from column 58 can be sent directly to the transalkylation reactor, bypassing the polyethylbenzene column 62. Normally, the weight ratio of the first portion supplied via line 88 directly to the transalkylation reactor to the second portion supplied initially via line 90 to the polyethylbenzene would be within the range of about 1:2 to about 2:1. However, the relative amounts may vary more widely to be within the range of a weight ratio of the first portion to the second portion in a ratio of about 1:3 to 3:1.

The molecular sieve catalyst employed in the critical phase alkylation reactor is a zeolite beta catalyst that can be a conventional zeolite beta modified by the inclusion of cerium as described below. The cerium-promoted zeolite beta catalyst will normally be formulated in extrudate pellets of a size of about ⅛-inch or less, employing a binder such as silica or alumina. A preferred form of binder is silica, which results in catalysts having somewhat enhanced deactivation and regeneration characteristics than zeolite beta formulated with a conventional alumina binder. Typical catalyst formulations may include about 20 wt. % binder and about 80 wt. % molecular sieve. The catalyst employed in the transalkylation reactor normally will take the form of a zeolite Y catalyst, such as zeolite Y or ultra-stable zeolite Y. Various zeolites of the Y and beta types are in themselves well known in the art. For example, zeolite Y is disclosed in U.S. Pat. No. 4,185,040 to Ward, and zeolite beta is disclosed in U.S. Pat. No. 3,308,069 to Wadlinger and U.S. Pat. No. 4,642,226 to Calvert et al.

The cerium-promoted zeolite beta employed in the critical phase alkylation reactor can be a zeolite beta of the type described in Wadlinger or Calvert, which has been modified by the inclusion of cerium in the crystalline framework. The cerium-promoted zeolite beta employed in the present invention can be based on a high silica/alumina ratio zeolite beta or a ZSM-12 modified zeolite beta as described in detail below.

Basic procedures for the preparation of zeolite beta are well known to those skilled in the art. Such procedures are disclosed in the aforementioned U.S. Pat. No. 3,308,069 to Wadlinger et al and U.S. Pat. No. 4,642,226 to Calvert et al and European Patent Publication No. 159,846 to Reuben, the disclosures of which are incorporated herein by reference. The zeolite beta can be prepared to have a low sodium content, i.e. less than 0.2 wt. % expressed as $Na_2O$ and the sodium content can be further reduced to a value of about 0.02 wt. % by an ion exchange treatment.

As disclosed in the above-referenced U.S. patents to Wadlinger et al., and Calvert et al, zeolite beta can be produced by the hydrothermal digestion of a reaction mixture comprising silica, alumina, sodium or other alkyl metal oxide, and an organic templating agent. Typical digestion conditions include temperatures ranging from slightly below the boiling point of water at atmospheric pressure to about 170° C. at pressures equal to or greater than the vapor pressure of water at the temperature involved. The reaction mixture is subjected to mild agitation for periods ranging from about one day to several months to achieve the desired degree of crystallization to form the zeolite beta. Unless steps are taken to minimize the alumina content, the resulting zeolite beta is normally characterized by a silica to alumina molar ratio (expressed as $SiO_2/Al_2O_3$) of between about 20 and 50.

The zeolite beta is then subjected to ion exchange with ammonium ions at uncontrolled pH. It is preferred that an aqueous solution of an inorganic ammonium salt, e.g., ammonium nitrate, be employed as the ion-exchange medium. Following the ammonium ion-exchange treatment, the zeolite beta is filtered, washed and dried, and then calcined at a temperature between about 530° C. and 580° C. for a period of two or more hours.

Zeolite beta can be characterized by its crystal structure symmetry and by its x-ray diffraction patterns. Zeolite beta is a molecular sieve of medium pore size, about 5–6 angstroms, and contains 12-ring channel systems. Zeolite beta is of tetragonal symmetry $P4_122$, a=12.7, c=26.4 Å (W. M. Meier and D. H. Olson Butterworth, *Atlas of Zeolite Structure Types*, Heinemann, 1992, p. 58); ZSM-12 is generally characterized by monoclinic symmetry. The pores of zeolite beta are generally circular along the 001 plane with a diameter of about 5.5 angstroms and are elliptical along the 100 plane with diameters of about 6.5 and 7.6 angstroms. Zeolite beta is further described in Higgins et al, "The framework topology of zeolite beta," *Zeolites*, 1988, Vol. 8, November, pp. 446–452, the entire disclosure of which is incorporated herein by reference.

The cerium-promoted zeolite beta employed in carrying out the present invention may be based upon conventional zeolite beta, such as disclosed in the aforementioned patent to Calvert et al. For a further description of procedures for producing zeolite beta useful in accordance with the present invention, reference is made to the aforementioned U.S. Pat. No. 3,308,069 to Wadlinger, U.S. Pat. No. 4,642,226 to Calvert, and U.S. Pat. No. 5,907,073 to Ghosh and EPA Publication No. 507,761 to Shamshoum, the entire disclosures of which are incorporated herein by reference.

The invention can also be carried out with a zeolite beta having a higher silica/alumina ratio than that normally encountered. For example, as disclosed in EPA Publication No. 186,447 to Kennedy, a calcined zeolite beta can be dealuminated by a steaming procedure in order to enhance the silica/alumina ratio of the zeolite. Thus, as disclosed in Kennedy, a calcined zeolite beta having a silica/alumina ratio of 30:1 was subjected to steam treatment at 650° C. and 100% steam for 24 hours at atmospheric pressure. The result was a catalyst having a silica/alumina ratio of about 228:1, which was then subjected to an acid washing process to produce a zeolite beta of 250:1. Various zeolite betas, such as described above, can be subject to extraction procedures in order to extract aluminum from the zeolite beta framework by extraction with nitric acid. Acid washing of the zeolite beta is carried out initially to arrive at a high silica/alumina ratio zeolite beta. This is followed by ion-exchanging cerium into the zeolite framework. There should be no subsequent acid washing in order to avoid removing cerium from the zeolite.

The procedure disclosed in EP 507,761 to Shamshoum, et al for incorporation of lanthanum into zeolite beta can be employed to produce the cerium promoted zeolite beta used in the present invention. Thus cerium nitrate may be dissolved in deionized water and then added to a suspension of zeolite beta in deionized water following the protocol disclosed in EP 507,761 for the incorporation of lanthanum into zeolite beta by ion exchange. Following the ion exchange procedure, the cerium exchanged zeolite beta can then be filtered from solution washed with deionized water and then dried at a temperature of 110° C. The powdered cerium exchanged zeolite beta can then be molded with an aluminum or silicon binding agent followed by extrusion into pellet form.

In experimental work carried out respecting the present invention alkylation reactor runs were carried out employing a single stage alkylation reactor. The reactor operated as a laboratory simulation of the single stage of a multiple stage reactor of the type illustrated in FIG. 3. In carrying out the experimental work a cerium promoted zeolite beta having a silica alumina ratio of 150 and a cerium/aluminum atomic ratio of 0.75 was employed. This catalyst was formed employing a silica binder. Comparative experimental work was employed carrying out a lanthanum promoted zeolite beta catalyst, also having a silica alumina ratio of 150 and having a lanthanum/aluminum atomic ratio of 1.0 formulated with a silica binder.

The cerium promoted zeolite beta was used in the alkylation reactor through five (5) regenerations for a total cumulative time of in excess of 140 days. Throughout the successive runs the inlet temperature or the reactor was about 300° C.±5° C. and the temperature at the outlet of the reactor was about 350° C.±10° C. resulting in an incremental temperature increase across the reactor of about 40–50° C. The reactor was operated at a inlet pressure of about 600 PSIG with a pressure gradient across the reactor of only a few pounds per square inch.

The lanthanum promoted zeolite beta was employed in a test run spanning about 55 days on line with regeneration of the catalyst at the conclusion of 20 days. The lanthanum promoted zeolite beta had a silica alumina ratio of 150 and a lanthanum/aluminum atomic ratio of 1.0.

Figure 4:
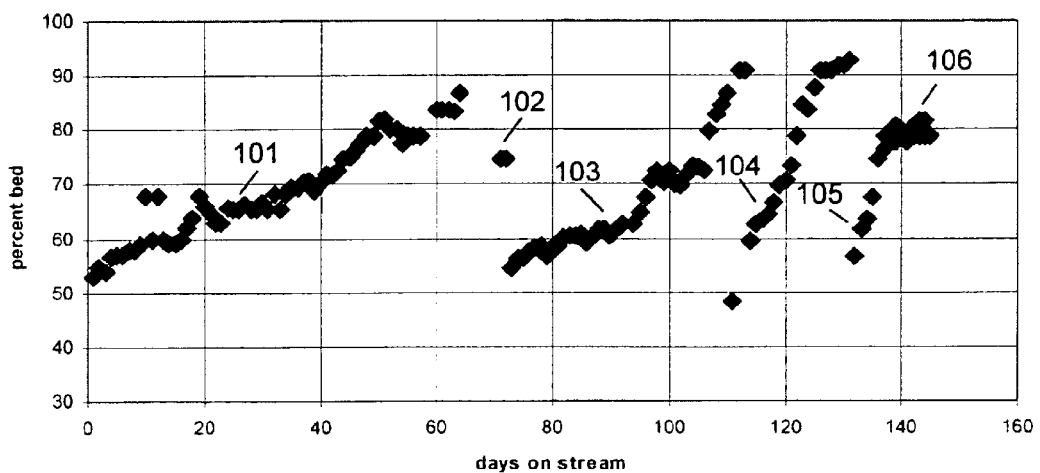
FIG. 4 is a graph illustrating the percent of bed used versus days on stream for an alkylation reaction carried out with a cerium modified zeolite beta.

The results of the experimental work carried out with the cerium beta catalyst are illustrated in FIGS. 4–11. Turning initially to FIG. 4 the percent of the bed used in the catalytic reaction is plotted on the ordinate versus the total cumulative days on stream on the abscissa. The percent of the catalyst bed was calculated based upon the maximum temperature sensed across the bed employing 6 temperature sensors spaced from the inlet to the outlet of the reactor. The percent of the bed used was calculated based upon the maximum temperature sensed at the temperature sensors across the bed. In FIG. 4 Curve 101 indicates the percent of bed used during the use of the fresh catalyst for an initial period of about 64 days. Curves 102, 103, 104, 105 and 106 show the results obtained after successive regeneration of the catalysts. Curve 106 indicates the results obtained for the catalyst after being regenerated by a high temperature regeneration procedure as described below in more detail with respect to FIG. 6.

Figure 5:
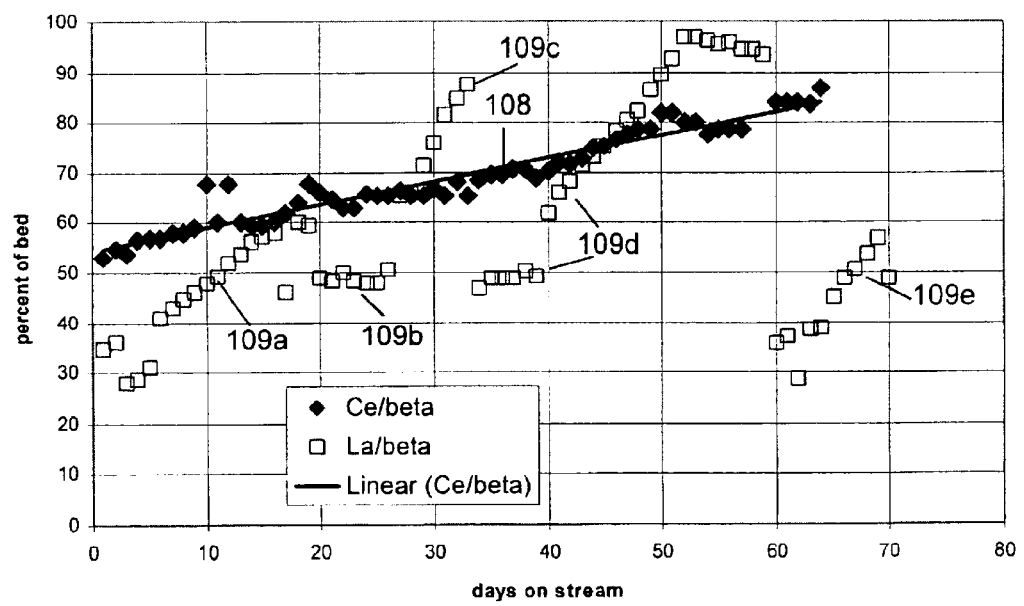
FIG. 5 is a graph showing the percent of bed used for both a cerium modified zeolite beta and a lanthanum modified zeolite beta.

FIG. 5 shows the catalyst bed used in the catalytic reaction as a function of days on stream for the fresh cerium beta catalyst indicated by Curve 108 corresponding to Curve 101 in FIG. 4 versus results obtained for lanthanum beta indicated by Curve 109. Curve 109 shows the results for fresh catalyst (109a), and successively regenerated lanthanum promoted beta catalyst indicated by Curves 109b, 109c, 109c, 109d and 109e. As can be seen from a comparison of Curves 108 and 109 the cerium promoted zeolite beta had a much higher stability over a prolonged period of time than exhibited by lanthanum beta over a series of successive regenerations.

Figure 6:
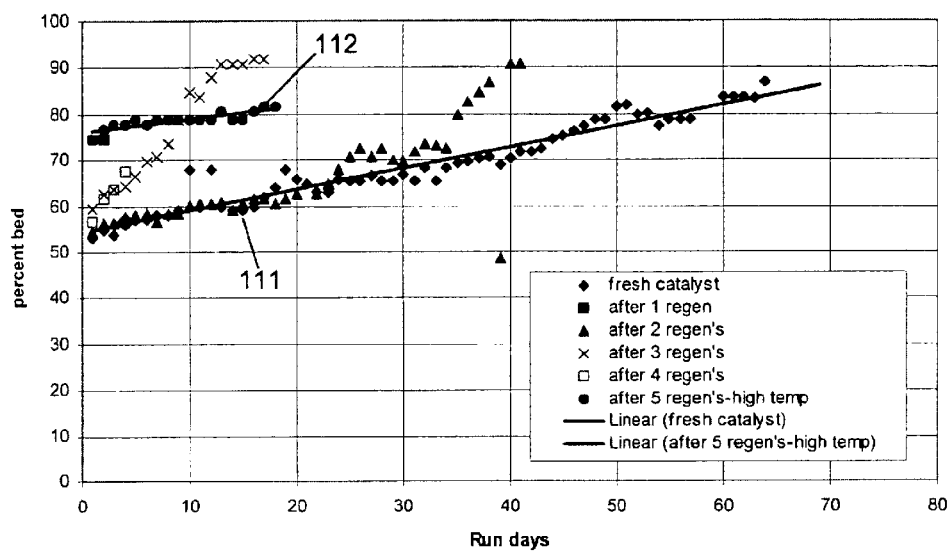
FIG. 6 is a graph showing the percent of bed used for cerium modified zeolite beta employed as a fresh catalyst and as a regenerated catalyst.

FIG. 6 shows the percent of bed used plotted on the ordinate versus run time and days plotted on the abscissa for the fresh catalyst and for the catalyst after each regeneration. In each case, the days elapsed after initiation with a fresh catalyst, and after initiation after each regeneration are shown. In FIG. 6 Curves 111 and 112 are linear plots for the fresh catalyst (Curve 111) and for the catalyst after five (5) regenerations with the last regeneration being carried out under high temperature conditions (Curve 112). As can be seen from an examination of the data shown in FIG. 6, after regeneration under normal temperature conditions at maximum temperature of about 475° C., the cerium promoted zeolite beta deactivated very rapidly. However, for the catalyst regenerated under the high temperature conditions in accordance with the present invention maximum temperature about 530° C. the catalyst deactivation rate corresponded generally to the catalyst deactivation observed for the fresh catalyst.

Figure 7:
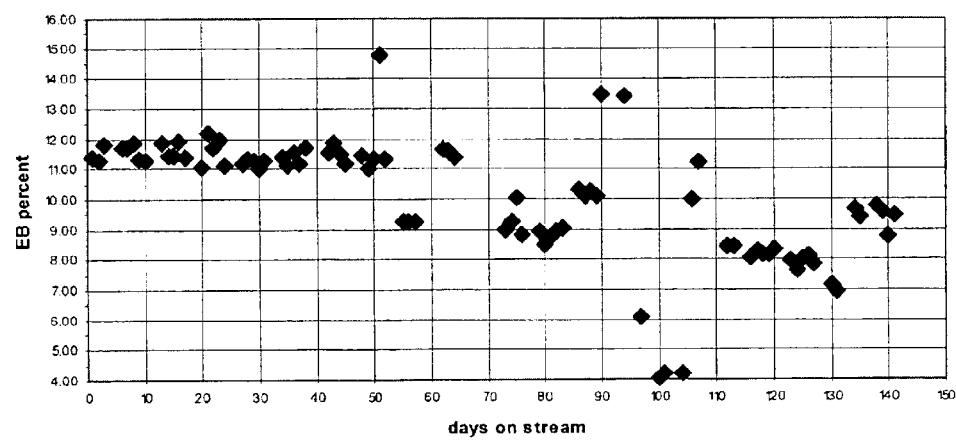
FIG. 7 is a graph showing an ethyl benzene yield versus days on stream for a cerium modified zeolite beta.

FIG. 7 shows the ethyl benzene yield, EB, in terms of percent conversion plotted on the ordinate versus the total cumulative days on stream for the cerium promoted zeolite beta. It will be recognized that the days on stream can be correlated with the regeneration data shown in FIG. 4. Thus, the fresh catalyst showed essentially a constant ethyl benzene conversion over the 64 day run carried out with the fresh catalyst. The anomalous results showing an ethyl benzene conversion at about 9% for days 55, 56 and 57 correlated with an inadvertent shutdown of the reactor.

Figure 8:
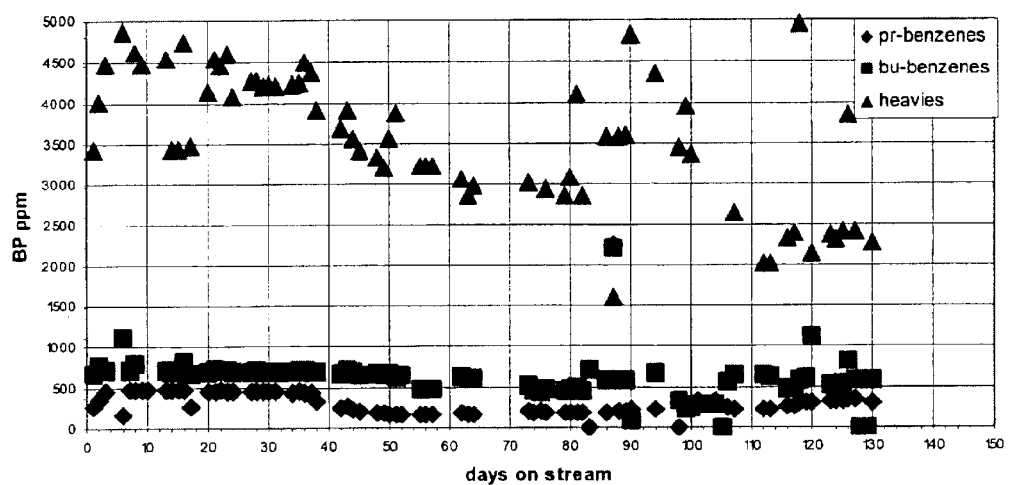
FIG. 8 is a graph illustrating by-product yield versus days on stream for a cerium modified zeolite beta.

FIG. 8 shows the by-product yield, BP, relative to ethyl benzene plotted in parts per million plotted on the ordinate versus for propyl benzene, butyl benzene and heavy components for the first 130 days of the run. As can be seen, the butyl benzene yield was less than 1000 ppm in the propyl benzene yield less than 500 ppm over the run time of 130 days. The heavy yield varied from about 5000 ppm to about 2000 ppm or slightly less. As discussed below these values are substantially better than the corresponding values observed for the lanthanum promoted zeolite beta.

Figure 9:
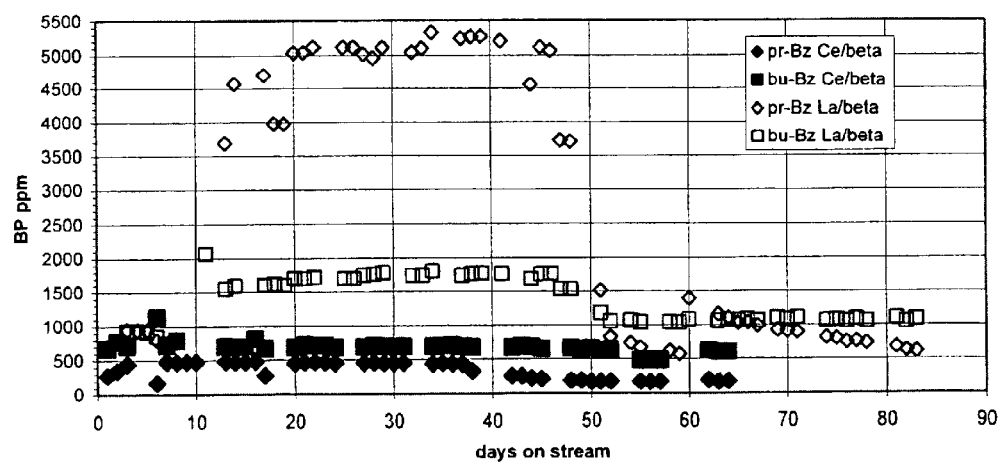
FIG. 9 is a graph showing comparative by-product yields for cerium modified zeolite beta and a lanthanum modified zeolite beta.
Figure 10:
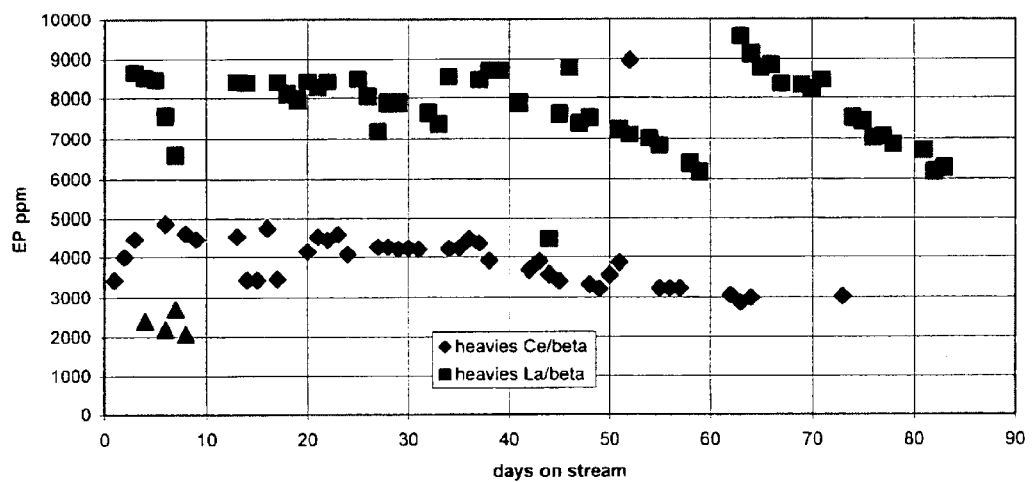
FIG. 10 is a graph showing a heavy by-product yield for cerium modified zeolite beta and lanthanum modified zeolite beta.

The comparative results for the propyl and butyl benzenes for the cerium promoted beta and the lanthanum promoted beta are illustrated in FIG. 9. FIG. 9 is a plot of the designated by-products in ppm versus relative to ethyl benzene plotted on the ordinate versus the days on stream on the abscissa. FIG. 10 shows corresponding data for the heavies for the cerium beta and the lanthanum beta. As can be seen from examination of the data in FIGS. 9 and 10 the cerium beta alkylation catalyst showed substantially lower by-products yields in each of the three (3) categories as was the case for the lanthanum promoted beta. Specifically, the composite by-product yield of propylbenzene and butylbenzene produced during super critical phase alkylation over the cerium-promoted zeolite beta was less than one-half of the corresponding by-product yield of propylbenzene and butylbenzene observed for the lanthanum-promoted zeolite beta.

Figure 11:
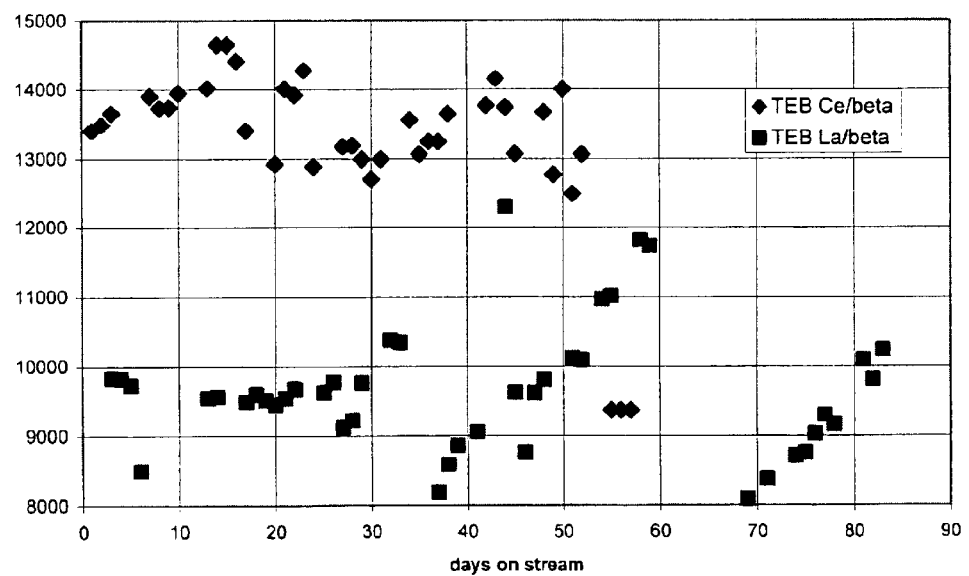
FIG. 11 is a graph illustrating the yield of triethyl benzene versus days of on stream for cerium modified zeolite beta and lanthanum modified zeolite beta.

FIG. 11 illustrates the triethyl benzene yield (TEB) in parts per million relative to ethyl benzene plotted on the ordinate versus the time on stream and days plotted on the abscissa. The data for the cerium beta catalyst was plotted for the first 52 days of the run carried out with the fresh catalyst. The data for the lanthanum beta zeolite shows results for lanthanum beta after a series of regenerations. As can be seen from an examination of FIGS. 9, 10 and 11 the substantially improved characteristics of the cerium promoted beta over the lanthanum promoted beta in terms of the heavy by-product yield comes at the expense of a moderately higher triethlybenzene production for the cerium beta.

Having described specific embodiments of the present invention, it will be understood that modifications thereof may be suggested to those skilled in the art, and it is intended to cover all such modifications as fall within the scope of the appended claims.

What is claimed:

1. A process for the production of ethylbenzene comprising:
   (a) supplying an aromatic feedstock containing benzene into a reaction zone and into contact with a cerium promoted zeolite beta molecular sieve alkylation catalyst in said reaction zone and containing cerium in an amount to provide a cerium/aluminum atomic ratio within the range of 0.25–5.0;
   (b) supplying ethylene to said reaction zone in an amount to provide a benzene/ethylene mole ratio within the range of 1–15;
   (c) operating said reaction zone at temperature and pressure conditions in which benzene is in the supercritical phase to cause ethylation of said benzene in the presence of said zeolite beta alkylation catalyst to produce an alkylation product containing ethylbenzene as a primary product with the attendant production of heavier alkylated by-products in a minor amount;
   (d) recovering said alkylation product from said reaction zone.

2. The process of claim 1 wherein the benzene to ethylene mole ratio is less than 10.

3. The process of claim 1 wherein the benzene to ethylene mole ratio is within the range of 3–8.

4. The method of claim 1 wherein said zeolite beta has a silica/alumina mole ratio within the range of 50–150.

5. The process of claim 1 wherein said zeolite beta has a cerium-aluminum atomic ratio within the range of 0.5–1.5.

6. The method of claim 1 wherein said alkylation zone is operated at temperature and pressure conditions to provide a composite by-product yield of propylbenzene and butylbenzene which is less than the corresponding composite by-product yield of propylbenzene and butylbenzene for a zeolite beta promoted with lanthanum at a lanthanum/aluminum atomic ratio at least equal to the cerium/aluminum atomic ratio of said cerium-promoted zeolite beta catalyst under the same temperature and pressure conditions.

7. The method of claim 1 wherein said alkylation reaction zone is operated at temperature and pressure conditions to provide a composite by-product yield of propyl benzene and butyl benzene which is no more than one-half of the corresponding by-product yield of propyl benzene and butyl benzene for a zeolite beta catalyst promoted with lanthanum at a lanthanum/aluminum atomic ratio at least equal to the cerium/aluminum atomic ratio of said catalyst under the same temperature and pressure conditions.

8. The process of claim 1 further comprising terminating the supply of said aromatic feedstock and ethylene to said reaction zone and thereafter regenerating said cerium promoted zeolite beta in said reaction zone by a regeneration procedure involving the injection of an oxygen containing gas into said reaction zone to provide a regeneration temperature in said reaction zone of at least 500° C. and thereafter reinstituting the supply of said aromatic feedstock and ethylene in the production of ethylbenzene in accordance with claim 1.

9. The process of claim 8 wherein said regeneration procedure is carried out to provide a maximum temperature within the range of about 515–550° C.

10. The process of claim 1 wherein the heavier alkylation by-products of said alkylation product comprise a polyalkylated aromatic component including diethyl benzene and further comprising:

supplying the alkylation product from the reaction zone to a recovery zone for the separation and recovery of ethylbenzene from the alkylation product and the separation and recovery of polyalkylated aromatic component including diethylbenzene;

supplying at least a portion of the polyalkylated aromatic component including diethylbenzene in said polyalkylated aromatic component to a transalkylation reaction zone containing a molecular sieve transalkylation catalyst, supplying benzene to said transalkylation reaction zone; and operating said transalkylation reaction zone under temperature and pressure conditions to cause disproportionation of said polyalkylated aromatic component to produce a disproportionation product having a reduced diethylbenzene content and an enhanced ethylbenzene content.

11. The process of claim 10 wherein the molecular sieve transalkylation catalyst in said transalkylation reaction zone is an intermediate pore size molecular sieve having an effective pore size equal to or greater than the effective pore size of said cerium promoted zeolite beta in said alkylation reaction zone.

12. The process of claim 11 wherein said transalkylation reaction zone contains a zeolite Y transalkylation catalyst and is operated under temperature and pressure conditions effective to maintain the polyalkylated aromatic component supplied to said transalkylation zone in the liquid phase.

13. The method of claim 12 wherein said alkylation zone is operated at temperature and pressure conditions to provide a composite by-product yield of propylbenzene and butylbenzene which is less than the corresponding composite by-product yield of propylbenzene and butylbenzene for a zeolite beta promoted with lanthanum at a lanthanum/aluminum atomic ratio at least equal to the cerium/aluminum atomic ratio of said cerium-promoted zeolite beta catalyst under the same temperature and pressure conditions.

14. A process for the production of ethylbenzene comprising:

(a) providing an alkylation reaction zone containing a cerium promoted zeolite beta aromatic alkylation catalyst;

(b) supplying a feedstock containing benzene in an amount of 90% of the aromatic content and ethylene to said alkylation reaction zone;

(c) operating said alkylation reaction zone at temperature and pressure conditions in which benzene is in the supercritical phase to cause ethylation of said benzene in the presence of said cerium promoted zeolite beta alkylation catalyst to produce an alkylation product comprising a mixture of benzene, ethylbenzene, and polyethyl benzene, (d) recovering the alkylation product from said alkylation reaction zone and supplying said product from said alkylation reaction zone to a recovery zone for the separation and recovery of ethylbenzene from the alkylated product and the separation and recovery of a polyalkylated aromatic component including diethylbenzene;

(e) supplying at least a portion of the polyalkylated aromatic component including diethylbenzene in said polyalkylated aromatic component to a transalkylation reaction zone containing a molecular sieve transalkylation catalyst, (f) supplying benzene to said transalkylation reaction zone; and (g) operating said transalkylation reaction zone under temperature and pressure conditions to cause disproportionation of said polyalkylated aromatic fraction to produce a disproportionation product having a reduced diethylbenzene content and an enhanced ethylbenzene content.

15. The process of claim 14 wherein said cerium promoted zeolite beta alkylation catalyst has a silica alumina mole ratio within the range of 50–150.

16. The process of claim 15 wherein said catalyst has a cerium/aluminum atomic ratio within the range of 0.25–1.25.

17. The process of claim 15 wherein the molecular sieve transalkylation catalyst in said transalkylation reaction zone is an intermediate pore size molecular sieve having an effective pore size equal to or greater than the effective pore size of said cerium promoted zeolite beta in said alkylation reaction zone.

18. The process of claim 17 wherein said transalkylation reaction zone contains a zeolite Y transalkylation catalyst and is operated under temperature and pressure conditions effective to maintain the polyalkylated aromatic component supplied to said transalkylation zone in the liquid phase.

19. The method of claim 14 wherein said cerium promoted zeolite beta is formed with a silica binder.

20. The method of claim 14 wherein said alkylation zone is operated at temperature and pressure conditions to provide a composite by-product yield of propylbenzene and butylbenzene which is less than the corresponding composite by-product yield of propylbenzene and butylbenzene for a zeolite beta promoted with lanthanum at a lanthanum/aluminum atomic ratio at least equal to the cerium/aluminum atomic ratio of said cerium-promoted zeolite beta catalyst under the same temperature and pressure conditions.

* * * * *